US007244390B2

(12) United States Patent
Bates et al.

(10) Patent No.: US 7,244,390 B2
(45) Date of Patent: *Jul. 17, 2007

(54) FUNGUS ABATEMENT SYSTEM

(75) Inventors: Perry C. Bates, Waterville, OH (US); Jim Stehlik, Waterville, OH (US)

(73) Assignee: SSCCS, LLC, A Limited Liability Company, State of Ohio, Waterville, OH (US)

( * ) Notice: Subject to any disclaimer, the term of this patent is extended or adjusted under 35 U.S.C. 154(b) by 118 days.

This patent is subject to a terminal disclaimer.

(21) Appl. No.: 10/855,256

(22) Filed: May 27, 2004

(65) Prior Publication Data

US 2005/0005616 A1 Jan. 13, 2005

(51) Int. Cl.
*A61L 2/00* (2006.01)

(52) U.S. Cl. .................. 422/24; 422/121; 454/231; 62/264; 96/225

(58) Field of Classification Search ............... 422/122, 422/120; 96/225; 62/264; 454/231
See application file for complete search history.

(56) References Cited

U.S. PATENT DOCUMENTS

| | | | | |
|---|---|---|---|---|
| 3,332,620 | A | 7/1967 | Streed | 236/44 |
| 4,484,517 | A * | 11/1984 | Amann | 99/474 |
| 4,829,882 | A | 5/1989 | Jackson | |
| 4,843,786 | A | 7/1989 | Walkinshaw et al. | 52/169.5 |
| 4,953,450 | A | 9/1990 | Remondino | 98/33.1 |
| 5,092,520 | A | 3/1992 | Lestage | 236/44 |
| 5,225,167 | A * | 7/1993 | Wetzel | 96/224 |
| 5,256,105 | A * | 10/1993 | Austin | 454/187 |
| 5,373,704 | A | 12/1994 | McFadden | 62/94 |
| 5,558,158 | A * | 9/1996 | Elmore | 165/122 |
| 5,891,399 | A | 4/1999 | Owesen | |
| 5,908,494 | A * | 6/1999 | Ross et al. | 96/356 |
| 5,987,908 | A * | 11/1999 | Wetzel | 62/259.1 |
| 6,021,953 | A | 2/2000 | Swan | 236/44 A |

(Continued)

OTHER PUBLICATIONS

Eggleston, Peyton A. Abstract of "Environmental control for fungal allergen exposure," Current allergy and asthma reports, (Sep. 2003) 3 (5) 424-9.*

(Continued)

*Primary Examiner*—E. Leigh McKane
(74) *Attorney, Agent, or Firm*—Young & Basile, P.C.

(57) ABSTRACT

An apparatus and methodology for abating fungi in a building supported on a ground surface and having an upper enclosed living space and a lower enclosed space beneath the upper enclosed space and proximate or beneath the ground. The apparatus includes a blower positioned in the lower enclosed space and having an air inlet and an air exhaust; a plurality of intake conduits having inlet ends adapted to open in the lower enclosed space proximate a lower boundary of that space and outlet ends connected to the inlet of the blower; a plurality of exhaust conduits having inlet ends connected to the exhaust of the blower and outlet ends discharging into the lower enclosed space; a plurality of ultraviolet lamps establishing germicidal killing zones intercepting and cleansing air moving from the lower enclosed space to the inlet of the blower; and a condenser positioned between the outlet ends of the intake conduits and the blower inlet, forming a part of a refrigerant loop, and serving to dehumidify the air moving from the outlet ends of the intake conduits to the inlet of the blower.

30 Claims, 11 Drawing Sheets

U.S. PATENT DOCUMENTS 6,619,063 B1 * 9/2003 Brumett .................. 62/264

OTHER PUBLICATIONS

UV-Aire Purifying System (2 sheets) retail information by Field Controls, prior art.
Voltarc Germicidal Lamps (4 sheets) array of sizes of lamps and characteristics, prior art.
Ultraviolet Light Fixtures (3 sheets) fixture information by Air Lights, prior art.
Aerobiological Engineering, Ultraviolet Germicidal Irradiation (6 sheets) presented by Penn State Architectural Engineering & Biology Departments, prior art.
Sylvania Engineering Bulletin 0-342, Germicidal and Short-Wave Ultraviolet Radiation (16 sheets) C.C. Mpelkas, Illumination Engineering Department, Sylvania, prior art.
Ultraviolet Susceptibility of BCG and Virulent Tubercle Bacilli (6 sheets) R.L. Riley M. Knight, and G. Middlebrook, prior art.
State of the Art Cleaning the Air, The Theory and Application of Ultraviolet Air Disinfection (9 sheets) Richard L. Riley and Edward A. Nardell, prior art.
Sylvania Product Catalog (6 sheets) containing germicidal lamp information, prior art.
Technical Bulletin, UV-Aire™ Field Report, (7 sheets), prior art Field Controls.
E-Z Breathe™ Ventilation System Rids Home of Pollutants, Provides Clean Air (2 sheets), prior art.
IESNA Lighting Handbook, Nonvisual Effects of Optical Radiation (7 sheets), prior art.
Influence of relative humidity on particle size and UV sensitivity of *Serratia marcenscens* and *Mycobacterium bovis* BCG aerosols; G. Ko, M.W. First, H.A. Burge, 2000 Harcourt Publishers Ltd., Department of Environmentsl Health, Harvard School of Public Health, Boston, MA 02115, USA (12 sheets).
Effect of Relative Humidity on the Inactivation of Airborne *Serratia marcenscens* by Ultraviolet Radiation, R. L. Riley and J.E. Kaufman, Department of Environmental Medicine, School of Hygiene and Public Health, The Johns Hopkins University, Baltimore, Maryland 21205 (8 sheets), prior art.

* cited by examiner

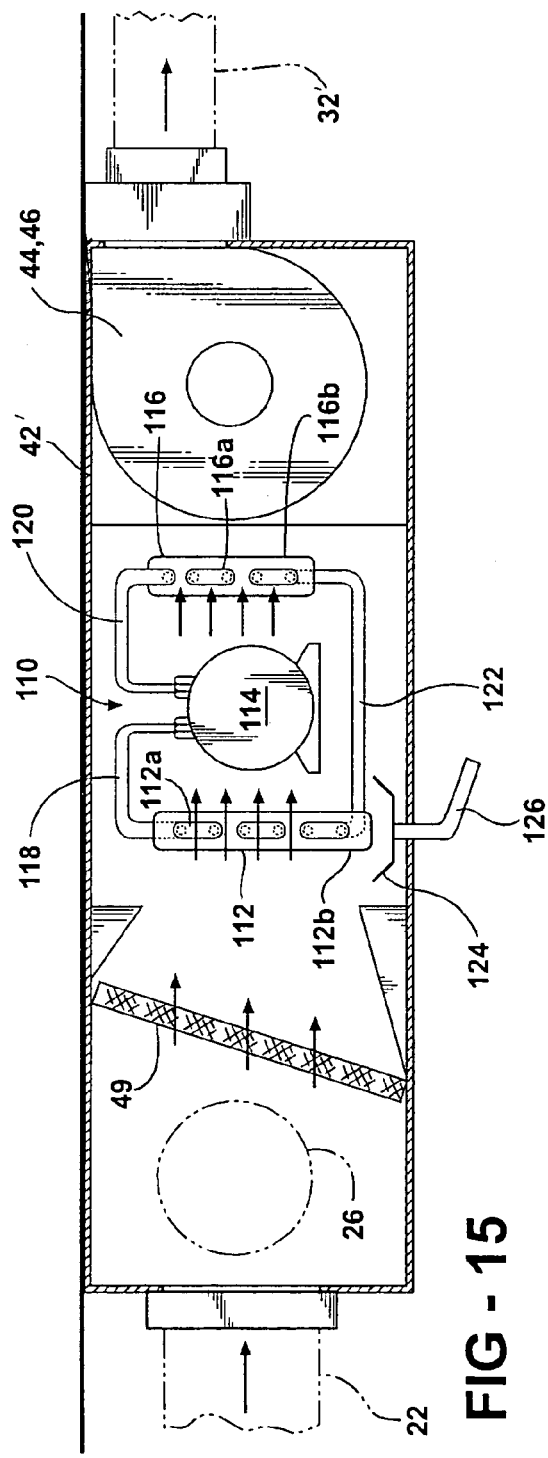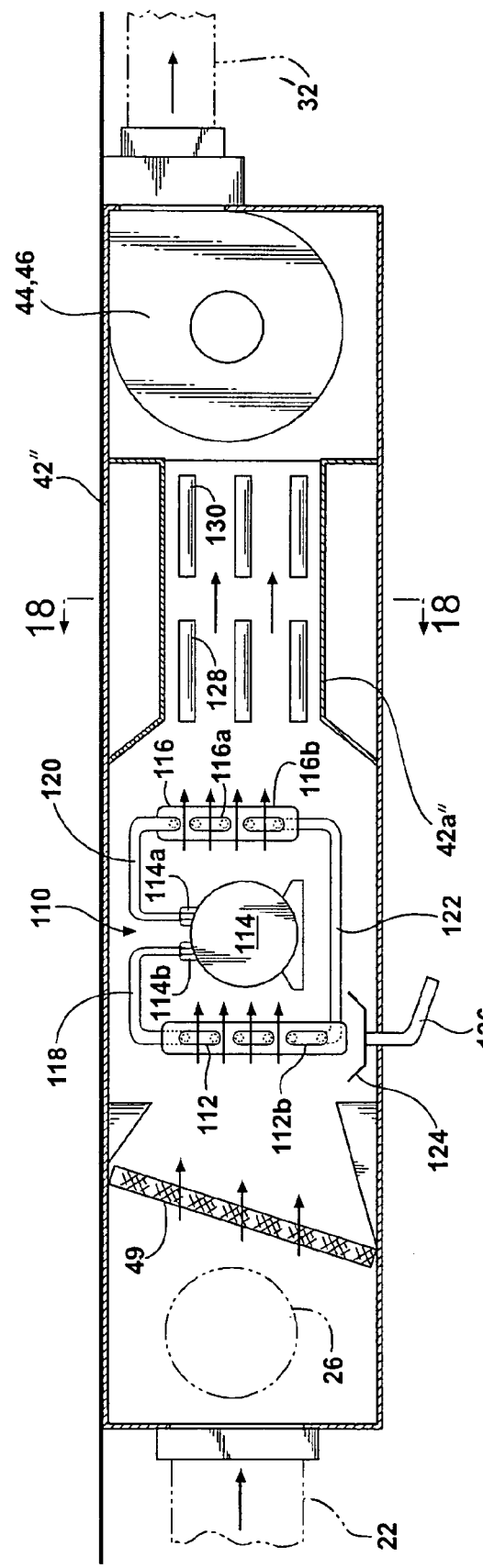

FUNGUS ABATEMENT SYSTEM

RELATED APPLICATIONS

This continuation-in-part application claims the priority of U.S. Provisional Patent Application Nos. 60/435,390 and 60/448,071, filed on Dec. 20, 2002 and Feb. 18, 2003, respectively and U.S. Utility patent application Ser. No. 10/733,904, filed on Dec. 11, 2003.

BACKGROUND OF THE INVENTION

The present invention relates to fungus abatement and more particularly to a system for use in preventing fungus from forming in a building structure such as a home or an office building.

Fungus is increasingly a problem in homes and office buildings. The fungus typically develops in unconditioned areas of the building such as basements or crawl spaces and is then spread by a natural upward flow of air and/or by the HVAC system to conditioned areas of the building where it contaminates the conditioned areas and generates occupant discomfort and health hazards.

SUMMARY OF THE INVENTION

The invention provides a method of maintaining a structure free of fungi. According to the invention method, a flow of air is created from an enclosed space within the structure, the flow of air is treated in a germicidal fashion, and the flow of air is treated in a dehumidifying fashion. This basic air handling and treating process results in a continual cleansing and dehumidifying of the air in the enclosed space to preclude contamination of other areas of the structure.

According to a further feature of the invention methodology, the flow of air is returned to the enclosed space after the germicidal treating step and after the dehumidifying treating step. The germicidal cleansing and the dehumidifying of the air conditions the air to a point where it is suitable for return to the enclosed space.

According to a further feature of the invention methodology, the germicidal treating step comprises creating a fungi killing zone in the enclosed space and passing the flow of air through the killing zone. This specific germicidal treating step effectively removes fungi from the air.

According to a further feature of the invention methodology, the killing zone comprises a zone in which the flow of air is subjected to radiant energy. This methodology provides a convenient means of creating the killing zone to destroy the fungi. In the disclosed embodiments of the invention the radiant energy comprises ultraviolet radiation.

In one embodiment of the invention methodology, the flow of air moves through the killing zone prior to its movement through the dehumidifier. In another version of the invention methodology, the air flows through the dehumidifier prior to its movement through the killing zone.

The invention also provides an apparatus for abating fungi in a structure having boundary walls defining a first enclosed space intended for human occupancy and a second enclosed space proximate the first enclosed space. The abatement apparatus comprises a blower unit, a source of radiant energy, and a dehumidifier. The blower unit has an air inlet and an air exhaust and is adapted to be positioned within the structure with the air inlet communicating with the second enclosed space, actuation of the blower unit being operative to create a flow of air from the second enclosed space into the blower unit inlet and thereafter discharge the air through the blower unit air exhaust. The source of radiant energy is adapted to be positioned to establish a fungi killing zone to intercept the flow of air moving from the second enclosed space to the inlet of the blower unit, and the dehumidifier is adapted to be positioned to intercept the flow of air moving from the second enclosed space to the inlet of the blower unit. This apparatus provides a ready and continuous cleansing and dehumidifying of the air in the second enclosed space and insures that all of the exhausted air is thoroughly dehumidfied and throughly treated with radiant energy to remove the fungi from the air.

In one embodiment of the invention apparatus, the radiant energy source comprises a series of ultraviolet lamps positioned in spaced locations within the second enclosed space and arranged to irradiate the air prior to its movement to the dehumidifier. In another embodiment of the invention apparatus, a housing is provided receiving the blower unit and the dehumidifier and the source of radiant energy is provided in the housing between the dehumidifier and the inlet of the blower unit so that the flow of air moving from the second enclosed space to the blower unit passes first through the dehumidifier and then through the killing zone established by the source of radiant energy.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIGS. 14, 15 and 16 are plan, side elevational, and perspective views of a modified form of the invention employing a dehumidifying apparatus; and FIGS. 17 and 18 are side elevational and cross-sectional views of a further modified form of the invention also employing a dehumidifying apparatus.

DETAILED DESCRIPTION OF THE PREFERRED EMBODIMENTS

Figure 1:
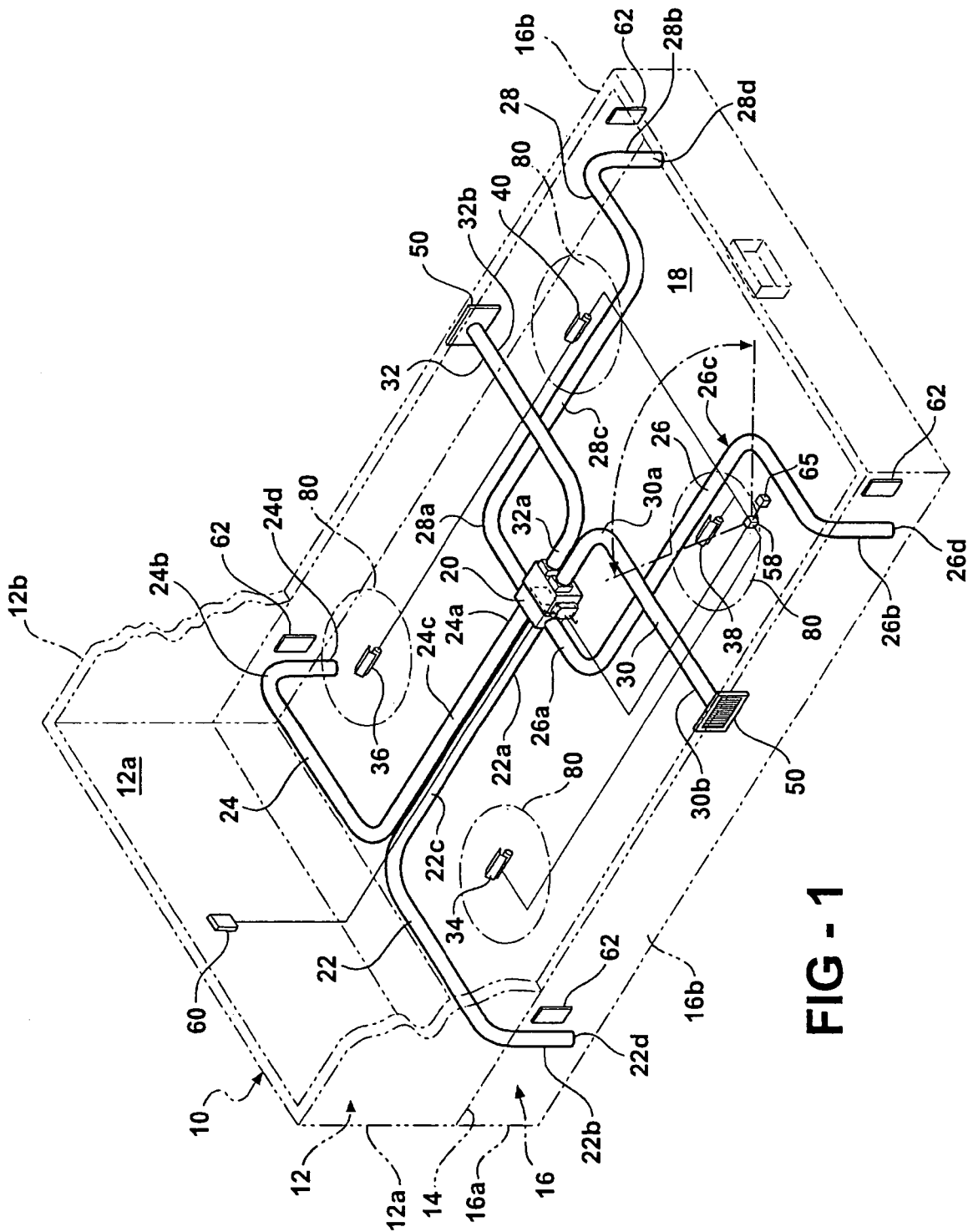
FIG. 1 is a perspective, fragmentary view of building having a crawl space employing a fungus abatement system according to the invention.
Figure 2:
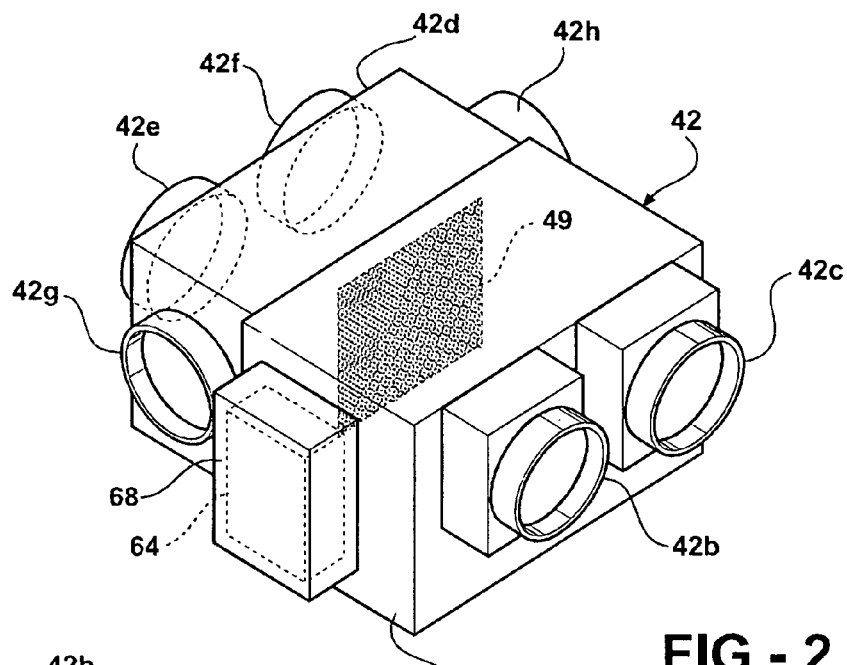
FIGS. 2, 3, 4 and 5 are perspective, plan, side elevation, and end views of a blower unit employed in the fungus abatement system.
Figure 3:
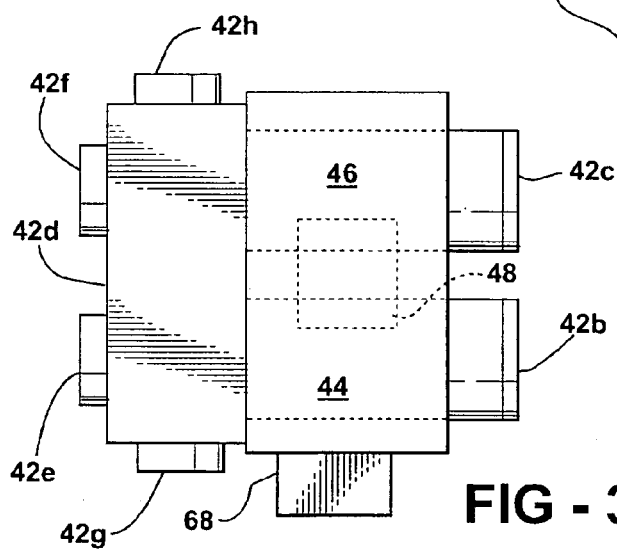
Figure 5:
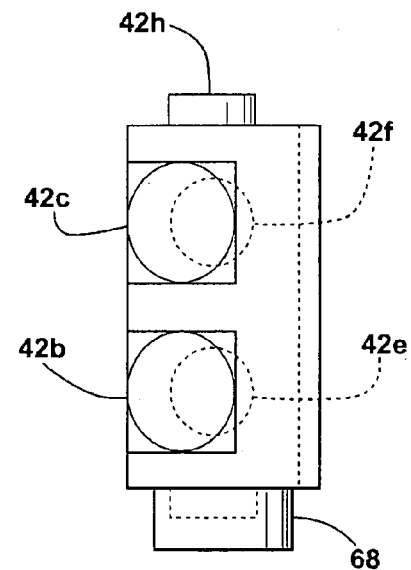
Figure 4:
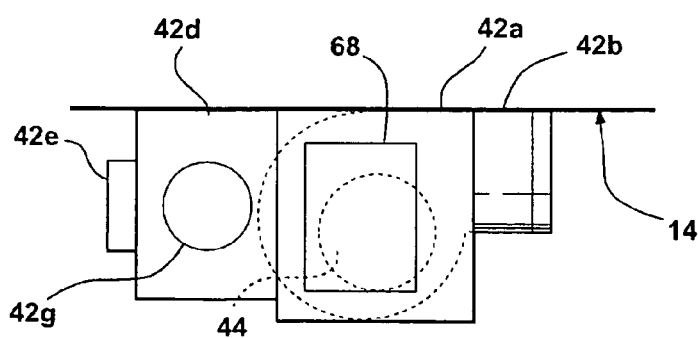
Figure 6:
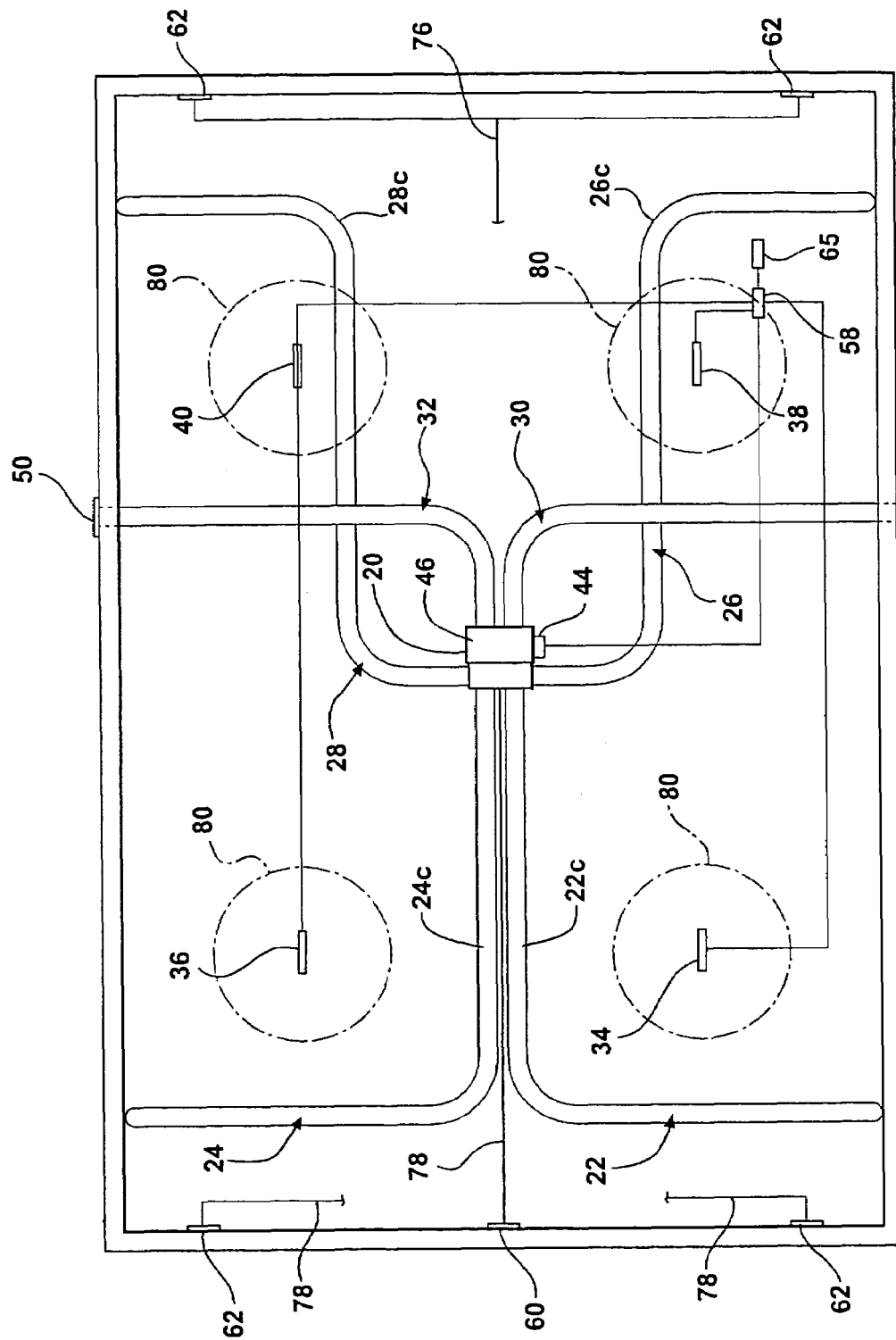
FIG. 6 is a plan view of the fungus abatement system.

The invention fungus abatement system is seen in FIGS. 1 and 6 installed in a building 10 of the type including an upper enclosed living area space 12, bounded by a floor 14, and a lower enclosed crawl space 16 beneath the upper enclosed space. Upper enclosed space 12 is defined by walls 12a and 12b as well as by floor 14 and crawl space 16 is defined by walls 16a and 16b as well as by a ground surface 18.

The fungus abatement system, broadly considered, includes a blower assembly 20, a plurality of air inlet conduits 22, 24, 26 and 28, a pair of exhaust conduits 30 and 32, and a plurality of germicidal units 34, 36, 38 and 40.

Blower assembly 20 includes a housing 42 and a pair of squirrel cage blowers 44 and 46.

Housing 42 (FIG. 2-5) has a sheet metal construction and is secured to the underface of floor 14 centrally within the crawl space 16. Housing 42 includes a main body portion 42a defining exhaust ports 42b and 42c, and a plenum chamber 42d positioned against main body portion 42a and defining intake ports 42e, 42f, 42g and 42h.

Squirrel cage blowers 44 and 46 are commonly driven by a central electric motor 48 positioned in housing main body portion 42a and may each comprise a unit available from Penn Zepher as Part Number Z102. Each blower 44, 46, will be understood to have an exhaust communicating with a respective exhaust port 42b, 42c and an intake communicating with plenum chamber 42d. Blower assembly 20 is preferably provided with a germicidal filter 49 positioned at the interface of plenum chamber 42d and the intakes of the blowers 44 and 46.

Intake conduits 22, 24, 26 and 28 each have an outlet end 22a, 24a, 26a, and 28a connected respectively to a housing port 42e, 42f, 42g and 42h; an inlet end 22b, 24b, 26b and 28b positioned respectively in the four corners of the crawl space; and an intermediate portion 22c, 24c, 26c and 28c interconnecting the inlet end and the outlet end of each conduit. Inlet ends 22b, 24b, 26b and 28b will be seen to be vertically disposed and will be seen to terminate in an inlet port 22d, 24d, 26d and 28d positioned proximate but spaced slightly above the ground surface 18. Intermediate portions 22c, 24c, 26c and 28c will be seen to comprise horizontal runs extending beneath floor 14 and interconnecting the respective inlet end and the respective outlet end of the respective conduit.

Exhaust conduits 30, 32 each define an inlet end 30a and 32a connected to a respective port 42b, 42c of housing 42 and an outlet end 30b and 32b communicating with a register or vent 50 positioned in opposite crawl space sidewalls 16b.

Figure 7:
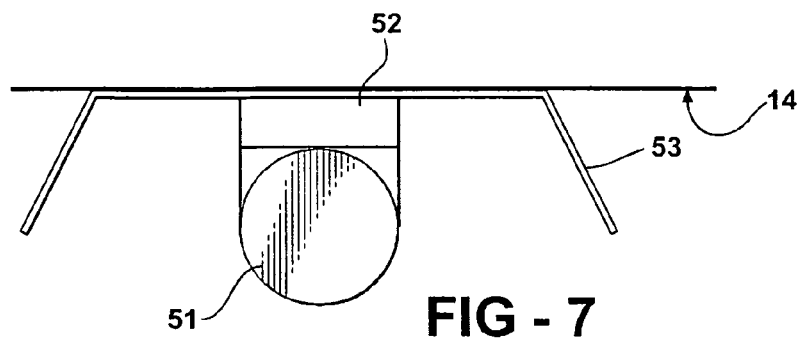
FIGS. 7 and 8 are cross-sectional views of germicidal lamp assemblies utilized in the fungus abatement system.
Figure 8:
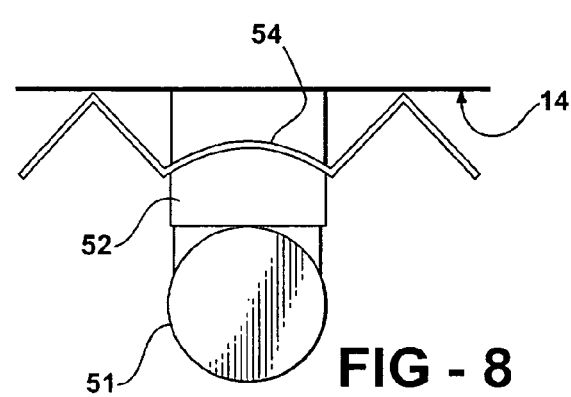

Germicidal units 34, 36, 38 and 40 are positioned on the underface of floor 14 in association with the inlet port of a respective intake conduit. Each germicidal unit may comprise, for example, a 15 watt ultraviolet germicidal lamp of the type available from Sylvania company as Part Number G15T8. Each germicidal lamp in known manner emits ultraviolet radiation in the wave length of 254 nm which has the effect of establishing a killing zone around each germicidal unit which will effectively kill any fungi carried by air passing through the killing zone. Each germicidal lamp comprises an elongated tube 51 and a base 52 to which the tube is suitably mounted. If desired, an overhead directional reflector may be provided with respect to at least certain of the lamps. The reflector may, for example, have an inverted trough configuration as seen at 53 in FIG. 7 or a gull wing configuration as seen at 54 in FIG. 8, depending upon the shape and size of the killing field that it is desired to establish in the vicinity of the tube 51. Preferably, however, no reflectors would be utilized in the crawl space embodiment of FIGS. 1-6. Rather, sufficient germicidal lamps would be provided to essentially flood the crawl space area with radiant energy.

The fungus abatement system of the invention further includes a motion detector 58, a control panel 60, a plurality of humidistats 62, and a controller 64.

Motion detector 58 may be installed in the crawl space 16 beneath the floor 14 and preferably has a 180° sweep. The detector may be of the type available from Desa International as Part Number 5411-ASL-5407A. This is a motion-on detector and is therefore used with a relay 65 to reverse the action of the motion detector to a motion-off detector. Relay 65 may be a 5 pin 6C895-7 type and may snap into a 5 pin base of the 6C898-1 type.

Control panel 60 may be positioned in upper enclosed living space 12 on wall 12a for ready access by occupants of living space 12.

A humidistat or humidistat trigger 62 may be installed in crawl space 16 proximate the inlet port 22d, 24d, 26d and 28d of each of the intake conduits whereby to sense the humidity of the air entering each of the intake conduits.

Controller 64 may be mounted, for example, in a controller housing 68 secured to a side face of blower housing 42.

Figure 9:
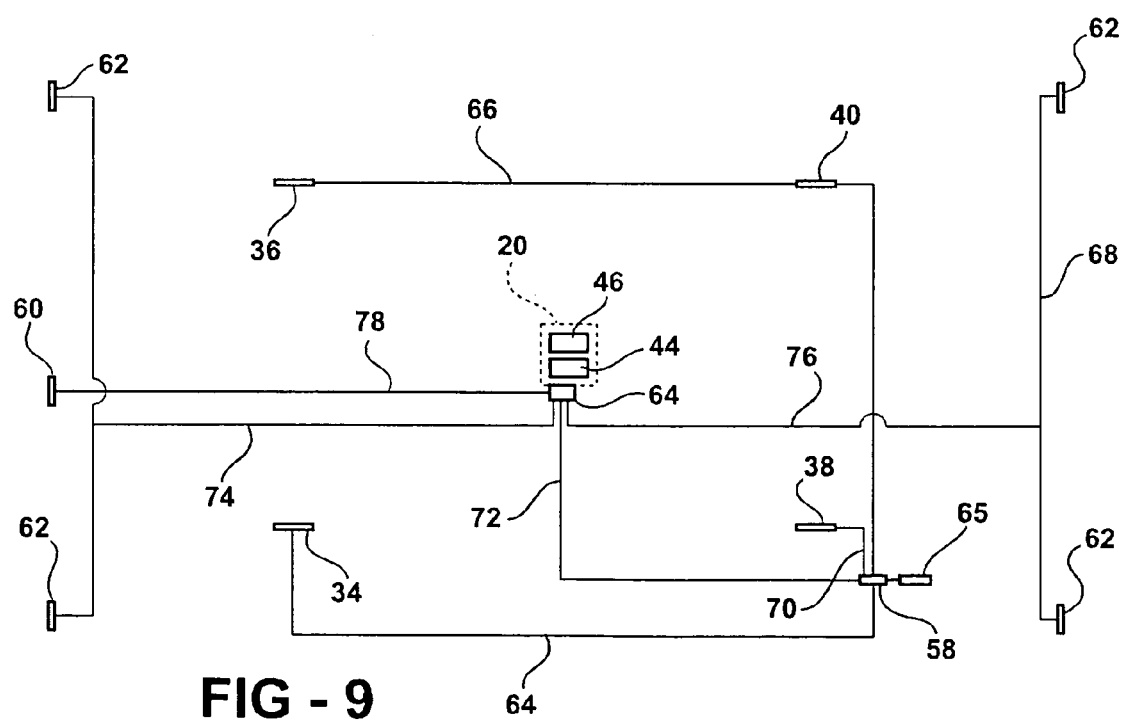
FIG. 9 is a wiring diagram for a fungus abatement system according to the invention.

As seen in the wiring diagram of FIG. 9, a lead 64 interconnects lamp 34 and motion detector 58; a lead 66 interconnects lamp 36 and lamp 40; a lead 68 interconnects lamp 40 and motion detector 60; a lead 70 interconnects lamp 38 and motion detector 60; a lead 72 interconnects motion detector 60 and controller 64; leads 74 and 76 interconnect thermostats 62 and controller 64; and a lead 78 interconnects control panel 60 and controller 64.

OPERATION

With control panel 60 calling for operation of the fungus abatement system, and assuming that the motion detector 58 does not detect the presence of anyone in the crawl space, the controller 64 functions to turn on the system and specifically functions to turn on the blowers 44, 46 and the lamps 34, 36, 38 and 40. Actuation of the blowers has the effect of drawing air from the crawl space 16 into the inlet ports 22d, 24d, 26d and 28d of the intake conduits for passage through the conduits to the plenum chamber 42d and thence through the squirrel cage blowers for discharge via the conduits 30 and 32 through the grills 50 to the exterior of the building. As the air moves respectively toward the inlet ports 22d, 24d, 26d and 28d of the intake conduits, the air passes through killing zones 80 established around each of the lamps 34, 36, 38, 40 so that effectively all of the air entering the inlet ports 22d of all of the conduits is first passed through a killing zone where the air is irradiated by the germinating lamp to kill any fungus or other contaminants carried by the air. The air passing through the intake conduits in turn passes through germicidal filter 49. The air thereafter moved outwardly through the exhaust conduits is thus essentially free of fungus and the air in the crawl space 16 is continuously purged of fungus so that the crawl space air, rather than rising upwardly laden with fungal contaminants into the conditioned air living area space above the crawl space, is cleansed within the crawl space and carried to a location outside of the building. Alternatively, the system may be programmed to cycle on and off dependent upon the readings provided by the humidistats 62. Specifically, as the humidity of one or more of the humidistats reaches a predetermined upper limit the controller functions to turn on the system and as the humidity reaches a predetermined lower limit as determined by the humidistats the blowers are turned off. Desirably, the ultraviolet lights remain on for a measured period of time following cessation of blower operation to insure that the stagnant air remaining in the crawl space is cleansed of fungi.

It will be understood that, depending upon the construction and porosity of the building, air will also be sucked downwardly from the conditioned air space 12 into the crawl space for discharge through the intake conduits and the exhaust conduits to the exterior of the building, thereby reversing the normal flow of air within the building.

It will further be understood that the efficiency of ultraviolet radiation is directly proportional to the density or the humidity of the air being treated. The denser or more humid the air, the slower the ultraviolet travel. Accordingly, by lowering humidity the efficiency of the germicidal units increases. In some scenarios involving exceptionally high humidity, it may be necessary to provide a separate dedicated dehumidifier to assist the invention system in maintaining a desired humidity level.

It will further be understood that, if the motion detector 58 detects movement in the crawlspace, the controller is appropriately signaled to turn off the system to preclude harm to living creatures in the crawlspace.

ALTERNATE EMBODIMENTS

Figure 10:
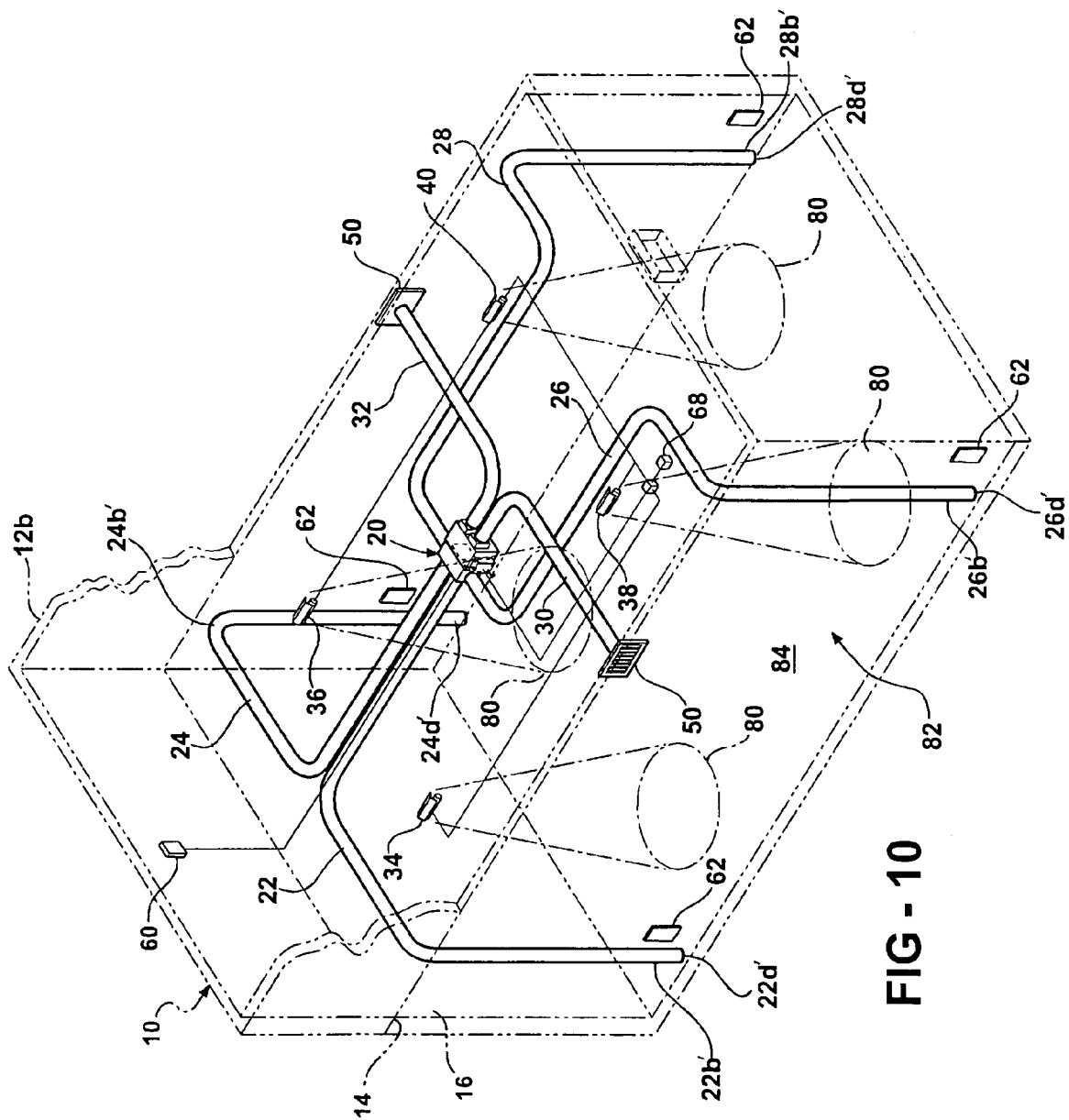
FIG. 10 is a perspective view showing the fungus abatement system of the invention utilized in a building having a full unfinished basement.

The fungus abatement system seen in FIG. 10 is intended for use with a building 10' having a full unfinished basement 82 including a floor 84. The system of FIG. 12, for use with a full unfinished basement, is identical to the system of FIG. 1, for use with a crawl space, except that the intake conduit lower ends 22$b'$, 24$b'$, 26$b'$, and 28$b'$ are extended vertically downwardly to position the conduit inlet ports 22$d'$, 24$d'$, 26$d'$ and 28$d'$ proximate the floor 84, and the humidistats 62 are moved downwardly to retain their positions proximate the inlet ports of the respective intake conduits whereby to monitor the humidity of the air entering the respective conduits. As with the crawl space configuration, sufficient germicidal lamps would be provided to essentially flood the basement area with radiant energy or, alternatively, at least certain of the ultraviolet lamps would be provided with directional reflectors. Lamps 34, 36, 38 and 40 are preferably mounted on the underface of floor 14.

Figure 11:
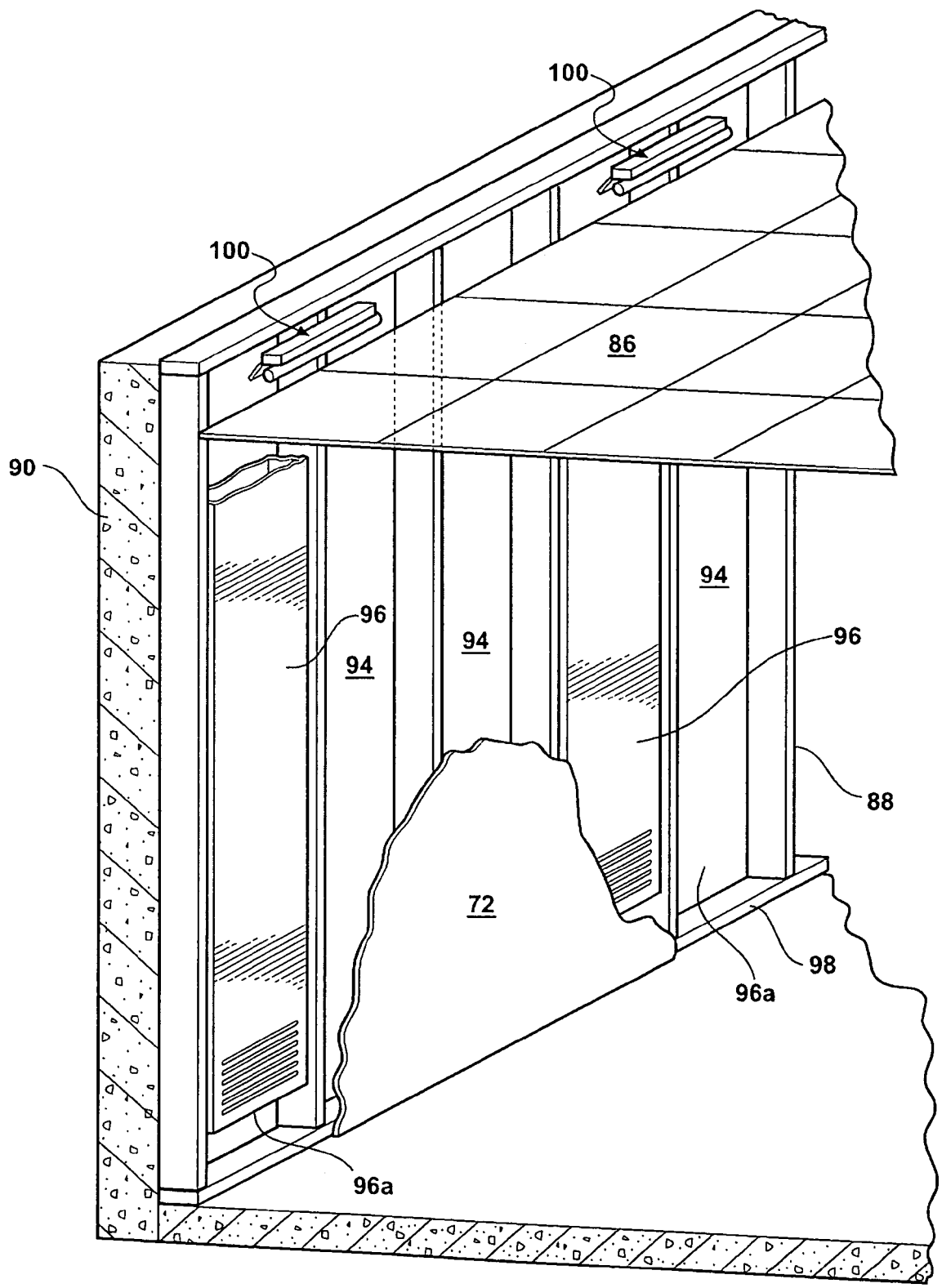
FIGS. 11-13 are fragmentary views showing the fungus abatement system of the invention utilized in a building having a full finished basement.
Figure 12:
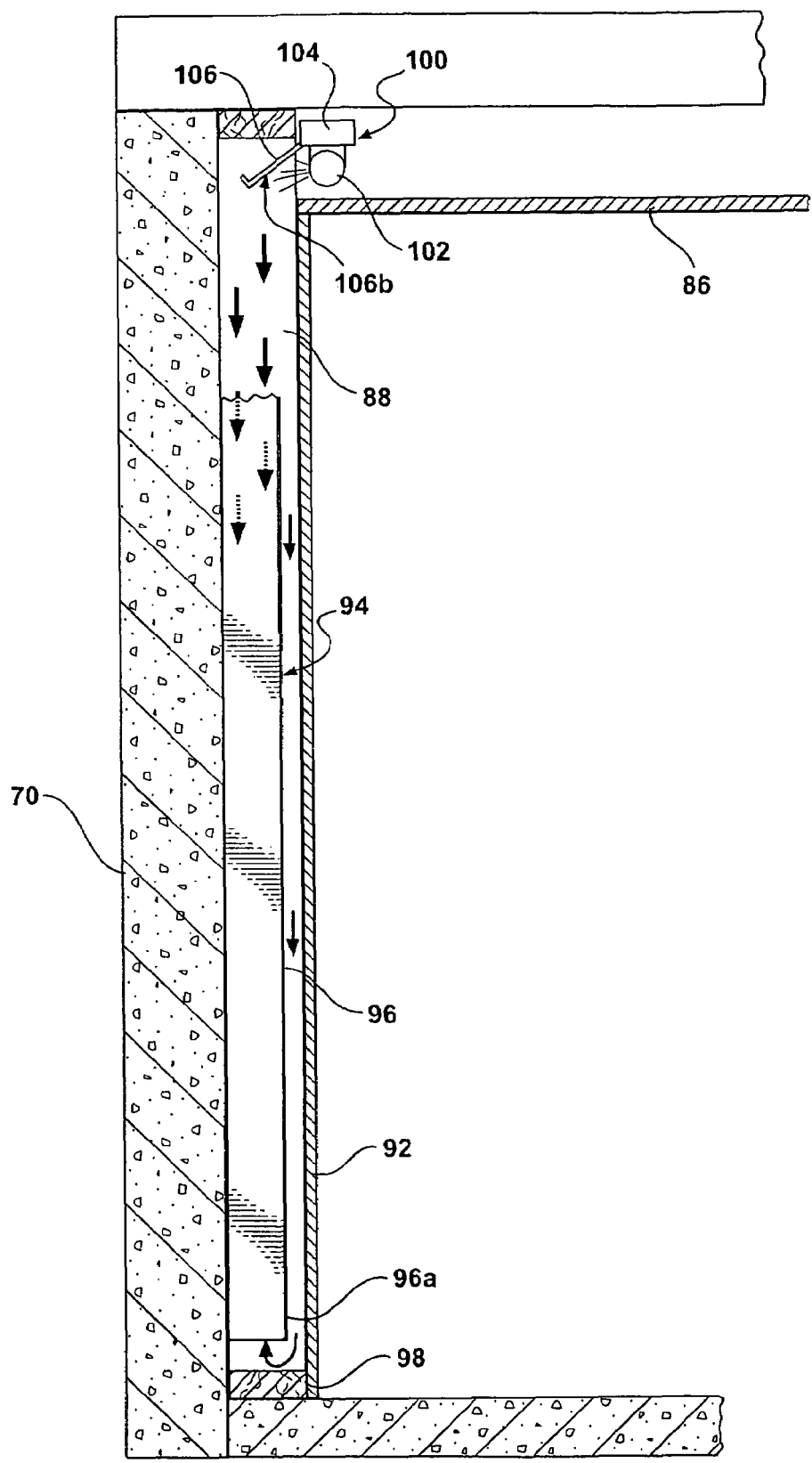
Figure 13:
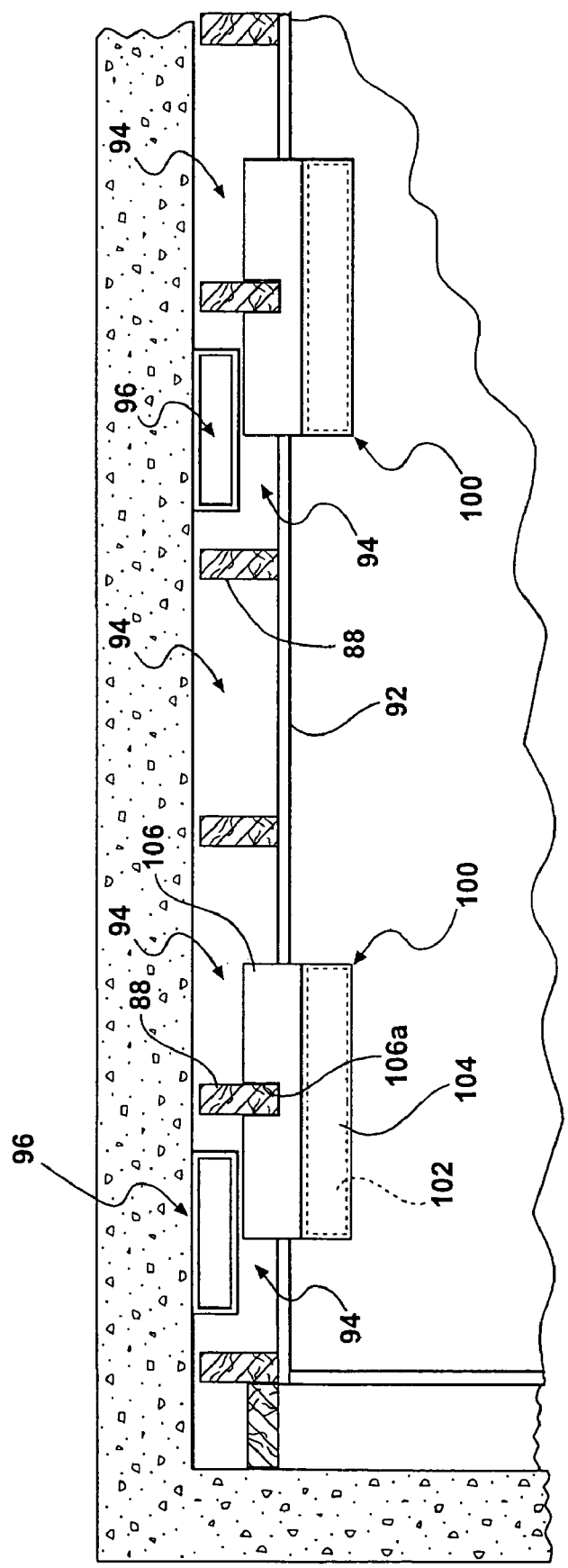

FIGS. 11-13 illustrate an arrangement for use in a full finished basement including a drop ceiling 86, studs 88 mounted against foundation wall 90, and dry wall or other paneling 92 mounted on the studs and defining dead air spaces 94 between the paneling and the foundation wall. Suitable HVAC equipment is provided so that the lower area within the paneling is provided year round with conditioned air, either heated or cooled. The fungus abatement system for the full finished basement of FIGS. 11-13 includes a plurality of vertical intake conduits 96 positioned between selected studs 88 with the open lower ends 96$a$ spaced above the sills 98 and a plurality of germicidal lamp units 100 positioned above the drop ceiling proximate to the perimeter of the basement. For example, and as shown, intake conduits 96 may be positioned around the perimeter of the basement on 48" centers and a germicidal lamp 100 may be provided in association with each intake conduit. Each germicidal lamp 100 may include an elongated tube 102, a base 104, and a reflector 106. Each lamp may be centered on a stud 88 and the reflector 106 may be notched at 106$a$ to fit over the stud. Each reflector 100 may be of the type available from Simkar Corporation as Part Number ARW20-SR and will be seen to provide an angled reflector surface 106$b$ which is operative to direct rays from the tube 102 downwardly into the dead air spaces 94 on either side of the stud over which the reflector is fitted so as to establish germicidal killing zones in the dead air spaces on either side of the stud over which the reflector is fitted.

It will be understood that the blower unit 20 in this finished basement embodiment is positioned centrally above the drop ceiling, that each conduit 96 is suitably connected to the intake of the blower unit, and that suitable humidistats (not shown) might be provided proximate the intake of the various conduits 96. In operation, following actuation of the blower unit and the germicidal lamps, any fungal matter in the dead air spaces 94 is killed by exposure to the ultraviolet killing zones established in the dead air spaces and the cleansed air is sucked upwardly through conduits 96 for discharge by the blower unit outside of the building. Since the studs 88 do not sealingly interface with the foundation wall but rather define significant spacing at the interface, air is free to move laterally from the dead air spaces in which a conduit is not positioned into a dead air space in which a conduit is positioned for entry into that conduit and discharge from the building. As the air moves laterally toward the intake of a conduit, it moves through a killing zone and is cleansed of fungal matter.

The forms of the invention heretofore described are open systems in which the conditioned air is exhausted outside of the associated building structure. The modified form of the invention seen in FIGS. 14-16 employs a dehumidifying apparatus to allow the unit to operate in a closed loop fashion with the blower discharge being returned to the enclosed space defined by a finished basement, for example, rather than being exhausted outside of the building structure.

Figure 14:
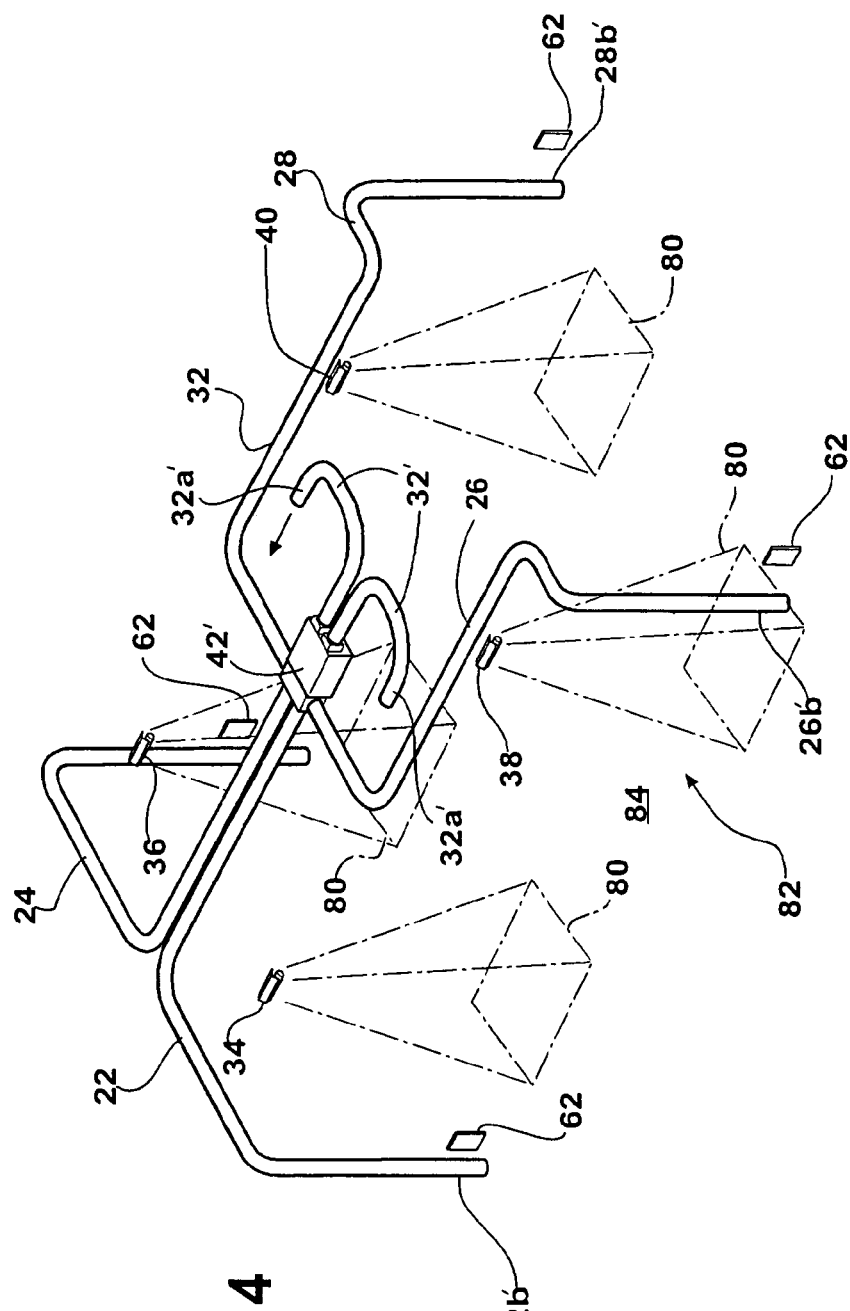
Figure 16:
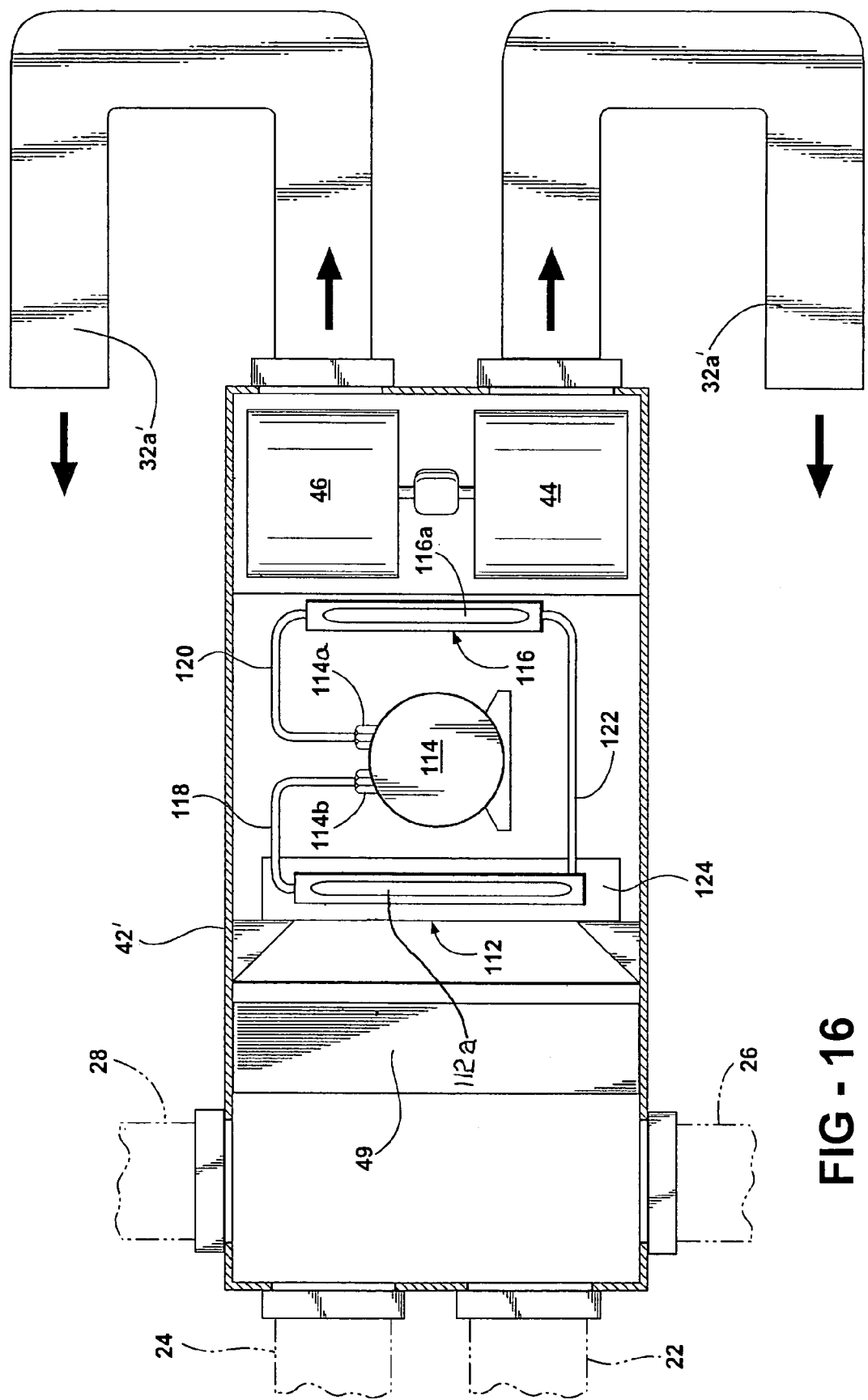

The apparatus seen in FIGS. 14-16 is generally similar to the apparatus seen in FIG. 10 and as such includes intake conduits 22, 24, 26 and 28 defining intake conduit lower ends 22$b'$, 24$b'$, 26$b'$ and 28$b'$ positioned proximate the floor of the associated enclosed space (for example a finished basement of a housing structure); a plurality of ultraviolet lamps 34, 36, 38 and 40 mounted at spaced locations on the underface of the floor of the enclosed space of the housing structure overlying the finished basement and establishing respective killing zones 80 positioned to intercept air moving from the finished basement space into the respective intake conduit lower ends, and a housing 42' receiving the outlet ends of the intake conduits 22, 24, 26 and 28 and housing the blowers 44 and 46.

However, and as best seen in FIG. 15, housing 42' also receives a dehumidifying apparatus 110 positioned within the housing between filter 49 and blowers 44, 46.

Dehumidifying apparatus 110 includes an evaporator 112, a compressor 114, and a condenser 116.

Evaporator 112, in known manner, may comprise a single continuous smooth wall tube 112$a$ extending in sinusoidal fashion within the housing 120$b$ of the evaporator and condenser 116, in known manner, may comprise a single continuous finned tube 116$a$ extending in sinusoidal fashion within the housing 116$b$ of the condenser. Compressor 114 may, for example, comprise a unit available from Danfoss as Model Number SE 15FPX; condenser 116 may, for example, comprise a unit available from Tecumseh as Model Number 508; the evaporator 112 may be formed of a length of 5/16" OD copper tubing received in a suitable housing; and the refrigerant may be R 134$a$. The refrigerant moves through the dehumidifier apparatus as indicated by the arrows and, specifically, leaves the outlet 114$a$ of the compressor as a high pressure vapor, moves through a conduit 120 to the inlet of the condenser, is transformed in the condenser to a liquid, flows as a liquid through a conduit 122 to the inlet of the evaporator, is transformed in the evaporator to a low pressure vapor, and moves through a conduit 118 to the inlet 114b of the compressor to complete the refrigerant loop.

In the operation of the embodiment of FIGS. 14-16, a flow of irradiated air from the enclosed space defined by the finished basement is delivered to plenum chamber 42d' of the housing 42' via intake conduits 22, 24, 26 and 28; thereafter moves through the filter 49; thereafter moves through evaporator 112 where it is cooled by the evaporation of the refrigerant and the resulting condensate collected in a drain pan 124 for discharge and collection via a drain tube 126; the cooled and dehumidified air thereafter moves through the condenser 116 where it serves to extract the superheat from the refrigerant and is heated; and the irradiated and dehumidified air flow is thereafter delivered to the blower units 44, 46 for discharge through exhaust conduits 32' which, rather than extending as in the FIG. 10 embodiment to registers 50 for discharge outside of the building, are configured to deliver the dehumidified and irradiated air back to the enclosed space via exhaust tube outlet ends 32a'.

Figure 18:
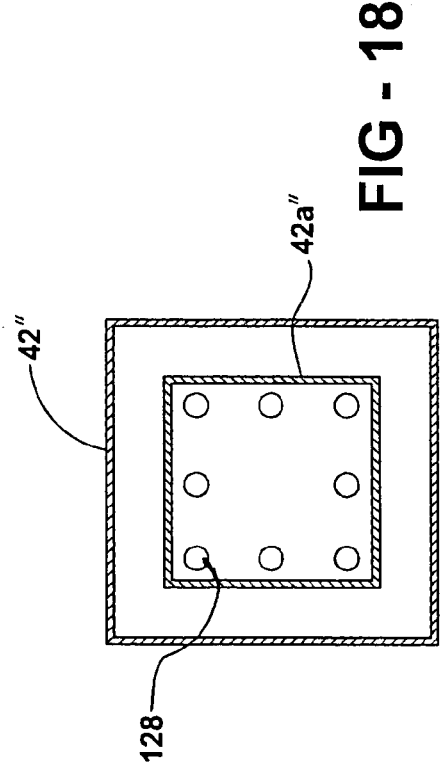

The modified apparatus as seen in FIG. 17 and 18 corresponds to the apparatus of FIGS. 14-16 with the exception that the killing zone for irradiation is established within the housing 42" between the dehumidifying apparatus 110 and the blower units 44, 46.

Specifically, the dehumidifying air leaving the dehumidifying unit 110, rather than flowing directly to the blowers 44, 46 as in the FIGS. 14-16 embodiment, instead is directed through a reduced diameter housing conduit 42a" where it is exposed to a series of ultraviolet lamps positioned within the conduit 42a" so that the flow of air arriving at the blowers 44, 46 is irradiated to remove fungi with the irradiation in this case taking place within the housing of the blower unit rather than taking place outside of the housing within the general area of the enclosed space as in the previous embodiments. Specifically, the flow of air leaving the dehumidifying unit first passes through a first killing zone established by a first series of circumferentially spaced ultraviolet lamps 128 positioned within the conduit 42a" and thereafter passes through a second killing zone established by a second series of circumferentially spaced ultraviolet lamps 130 positioned within the conduit 42a". As in the case of the 14-16 embodiment, the irradiated and dehumidified air leaving the blowers 44, 46 is returned via conduits 32' to the enclosed space rather than being discharged outside of the building. As noted, in the embodiment of FIGS. 17 and 18 the ultraviolet lamps 34, 36, 38 and 40 and their associated killing zones 80, are eliminated since the irradiation is now performed within the blower unit housing.

SPECIFICATIONS

The number sizing and location of the various components of the mold abatement system will of course depend on whether a crawl space is being treated or a full basement is being treated and will of course in each case further depend on the size of the crawl space or the full basement.

As an example, for a crawl space with dimensions of 26' wide by 42' long and 36" deep for a total of 3,276 cubic feet, the blower assembly 20 would have a 638 cfm capacity and would serve to establish a system static pressure of 0.375 inches, and would operate on 3.6 amps. This arrangement would serve to change the air within the crawl space ten times per hour. As previously noted, blowers 44 and 46 in this crawl space configuration may comprise units available from Penn Zepher as Part Number Z102. These blower units would also be satisfactory for use in the full finished basement embodiment of FIGS. 11-13.

As a further example, for a full unfinished basement 8' deep by 26' wide by 42' long, resulting in 8,736 cubic feet of space, a 950 cfm blower assembly 20 would be required operating at 0.8375 inches system static pressure. This arrangement would serve to change the air within the basement 5.868 times per hour. Blowers 44 and 46 in this full basement configuration may comprise units available from Penn Zepher as Part Number Z121.

The invention will be seen to provide an efficient and inexpensive means of precluding the contamination of the living areas of a building by fungi. The embodiments of the invention illustrated in FIGS. 1-13, where the irradiated air is exhausted to a location outside of the building structure, are best suited for crawl space applications or applications where the basement, while full size, is not primarily used for human habitation, and the embodiments seen in FIGS. 14-18, where the air is dehumidified prior to discharge from the blower units, are best suited for use in full basements that are finished and where regular human habitation is contemplated.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law. For example, the term fungi as used in the specification and appended claims will be understood to include germs, parasites, spores, bacteria, mold, rust, mildew, smuts, mushrooms and other airborne contaminants. As a further example, the particular reflector configuration, if any, employed in association with the ultraviolet lamps will vary depending upon the nature and configuration of the space being treated. As a yet further example, although the invention has been described with reference to the germicidal treatment of air in a lower enclosed space of a building, it also has applicability in certain situations to the germicidal treatment of air in an upper enclosed space of a building. As a yet further example, although the invention has been described with reference to treatment of air in a building, it may also have applicability to the treatment of air in structures other than buildings.

What is claimed is:

1. A method of maintaining an enclosed space in a building structure free of fungi comprising the steps of:
providing a housing having an inlet end and an outlet end and a passage extending between the inlet end and the outlet end;
positioning the housing within the enclosed space;
positioning a blower unit proximate the outlet end of the housing;
positioning an evaporator in the passage between the blower unit and the housing inlet end;
positioning a condenser in the passage between the evaporator and the blower unit;
positioning a compressor in the passage between the evaporator and the condenser;
operatively connecting the compressor to the evaporator and the condenser within the passage to form a closed circuit refrigerant loop totally contained within the passage; and
positioning a germicidal device in the passage between the condenser and the blower unit, the blower unit functioning to draw fungi infected air from the enclosed space, draw it through the inlet end of the housing, pass it successively over the evaporator, the compressor, the condenser and the germicidal device, and discharge the germicidally treated air into the enclosed space.

2. A method according to claim 1 wherein the housing includes a plenum proximate the inlet end and a plurality of intake conduits are provided having outlet ends connected to the plenum and inlet ends positioned at spaced locations within a lower region of the enclosed space.

3. A method according to claim 2 wherein the inlet ends of the intake conduits are positioned in spaced relation proximate a floor surface of the enclosed space.

4. A method according to claim 1 wherein the germicidal treating step comprises:
creating a fungi killing zone in the passage; and
passing the flow of air through the killing zone.

5. A method according to claim 4 wherein the killing zone comprises a zone in which the flow of air is subjected to ultra violet radiation.

6. A method according to claim 1 wherein the germicidal device comprises a plurality of elongated ultraviolet lamps arranged in parallel spaced relation in the passage between the condenser and the blower with a lengthwise axis of each lamp extending substantially parallel to the direction or air flow through the passage.

7. A method according to claim 1 wherein:
the building structure is situated on a ground surface and has an upper enclosed space and a lower enclosed space beneath the upper enclosed space and proximate or beneath the ground surface;
the fungi infected air is drawn through the inlet end of the housing from the lower enclosed space; and
the germicidally treated air is discharged into the lower enclosed space.

8. A method according to claim 1 wherein:
the building has a first enclosed space intended for human occupancy and a second enclosed space proximate the first space;
the housing is positioned in the second enclosed space;
the fungi infected air is drawn through the inlet end of the housing from the second enclosed space; and
the germicidally treated air is discharged into the second enclosed space.

9. An apparatus for abating fungi in a structure having boundary walls defining an enclosed space the apparatus positionable within the enclosed space and comprising:
a housing having an inlet end and an outlet end and defining a passage extending between the inlet end and the outlet end;
a blower unit positioned proximate the outlet end of the housing and having an air inlet communicating with the passage and an air exhaust communicating with the enclosed space;
an evaporator positioned within the passage between the blower unit air inlet and the inlet end of the housing;
a condenser positioned within the passage between the evaporator and the blower unit air inlet;
a compressor positioned in the passage between the evaporator and the condenser and operatively connected within the passage to the evaporator and the condenser to form a closed circuit refrigerant loop totally contained within the passage; and
a germicidal device positioned in the passage between the condenser and the blower unit air inlet, the blower unit functioning with the apparatus positioned in the enclosed space to draw fungi contaminated air from the enclosed space through the inlet end of the housing, through the evaporator, over the compressor, through the condenser, through the germicidal device, and through the blower unit air inlet for discharge of dehumidified and fungi free air through the blower unit air exhaust back to the enclosed space.

10. An apparatus according to claim 9 wherein the germicidal device comprises a plurality of elongated ultraviolet lamps arranged in parallel spaced relation in the passage between the condenser and the blower with the lengthwise axis of each lamp extending substantially parallel to the direction of air flow through the passage.

11. An apparatus according to claim 10 wherein the apparatus further includes an exhaust conduit having an inlet end connected to the air exhaust of the blower unit and an outlet end opening in the enclosed space.

12. An apparatus according to claim 10 wherein the lamps are arranged in circumferentially spaced relation in the passage and the air flow occurs within the passage substantially inboard of the circumferentially spaced lamps.

13. An apparatus according to claim 9 wherein the apparatus includes a filter at the inlet end of the housing and the passage extends in a substantially straight line between the filter at the inlet end of the housing and the blower at the outlet end of the housing.

14. A structure comprising:
boundary walls defining a first enclosed air space intended for human occupancy and a second enclosed air space proximate the first air space and having a ceiling and a floor surface;
a housing positioned beneath the ceiling of the second enclosed space having an inlet end and an outlet end and defining a passage extending between the inlet end and the outlet end;
a blower unit positioned proximate the outlet end of the housing and having an air inlet communicating with the passage and an air exhaust communicating with the second enclosed space;
an evaporator positioned in the passage between the blower unit air inlet and the inlet end of the housing;
a condenser positioned in the passage between the evaporator and the blower air inlet;
a compressor positioned in the passage between the evaporator and the condenser and operatively connected within the passage to the evaporator and the condenser to form a closed circuit refrigerant loop totally contained within the passage; and
a germicidal device positioned in the passage between the condenser and the blower unit air inlet, the blower unit functioning to draw fungi contaminated air from the second enclosed space, through the inlet end of the housing, through the evaporator, through the condenser, over the compressor, through the germicidal device, and to the blower unit air inlet for discharge of dehumidified fungi free air through the blower unit air exhaust back to the second enclosed space.

15. A structure according to claim 14 wherein:
the housing includes a plenum proximate the inlet end of the housing;
the structure further includes a plurality of intake conduits having outlet ends connected to the plenum and inlet ends positioned at spaced points within the second enclosed space;
the inlet end of each intake conduit opens in the second enclosed space proximate the floor surface of the second enclosed space; and the structure further includes an exhaust conduit having an inlet end connected to the blower unit air exhaust and an outlet end communicating with an upper region of the second enclosed space.

16. A structure according to claim 14 wherein the germicidal device comprises a plurality of elongated ultraviolet lamps arranged in parallel spaced relation in the passage between the condenser and the blower with the lengthwise axis of each lamp extending substantially parallel to the direction of air flow through the passage.

17. A structure according to claim 14 wherein the structure further includes means for providing conditioned air to the first enclosed space.

18. A method of maintaining a building structure free of fungi, the building having an enclosed space within the structure defined by a floor surface, side walls and a ceiling, the method comprising the steps of:
providing a housing having an inlet end and an outlet end;
providing a blower at the outlet end of the housing having an inlet for receiving air flowing through the housing and an outlet for discharging air delivered to the blower inlet;
providing a plenum at the inlet end of the housing;
providing a plurality of free standing elongated tubular intake conduits having outlet ends connected to the plenum and free standing inlet ends extending downwardly from the outlet ends;
positioning the housing in an upper region of the enclosed space with the conduits positioned in free standing relation in spaced relation to the side walls and with the free standing inlet ends of the conduits opening at spaced locations proximate but spaced above the floor surface and distributed over the entire area of the floor surface whereby to effectively collect air from the entire enclosed space proximate the floor surface in response to operation of the blower and draw the collected air through the conduits and through the housing for delivery to the blower inlet;
subjecting the air flowing from the enclosed space to the blower to a germicidal treatment; and
discharging the collected and germicidally treated air from the blower outlet.

19. A method according to claim 18 wherein the germicidal treating step comprises:
creating a fungi killing zone; and
passing the flow of air through the killing zone.

20. A method according to claim 19 wherein the killing zone comprises a zone in which the flow of air is subjected to ultraviolet radiation.

21. An apparatus for abating fungi in a building structure having an enclosed space including side walls, a ceiling, and a floor surface, the apparatus comprising:
a housing having an inlet end and an outlet end;
a plenum defined at the inlet end of the housing;
a blower unit positioned at the outlet end of the housing and having an air inlet for receiving air flowing through the housing and an air exhaust for discharging air delivered to the blower unit inlet;
a plurality of elongated free standing tubular conduits each having an outlet end communicating with the plenum and a free standing inlet end extending downwardly from the outlet end, the conduits being configured such that, with the housing positioned in an upper region of the enclosed space, the conduits are positioned in free standing relation in the enclosed space in spaced relation to the side walls and the free standing inlet ends of the conduits are positioned at spaced locations proximate but spaced from the floor surface, the inlet ends being distributed over the entire area of the floor surface, actuation of the blower unit being operative to effectively collect air from the entire area of the floor surface, draw it through the conduits to the plenum, and draw it through the housing for discharge into the enclosed space; and
a source of radiant energy adapted to be positioned-to establish a fungi killing zone to intercept collected air moving through the conduits and the housing from the floor surface to the blower unit.

22. A structure according to claim 21 wherein the source of radiant energy comprises an ultraviolet lamp.

23. An apparatus according to claim 22 wherein the apparatus further includes an exhaust conduit having an inlet end connected to the exhaust of the blower unit.

24. An apparatus according to claim 22 wherein each intake conduit has a horizontal run connected to the plenum and a vertical run extending downwardly from the horizontal run to position the inlet end of the intake conduit proximate the floor surface of the enclosed space.

25. A structure comprising:
boundary walls defining a first enclosed air space intended for human occupancy and a second enclosed air space proximate the first air space and having side walls and a floor surface;
a housing positioned in an upper region of the second enclosure and having an inlet end and an outlet end;
a plenum defined at the inlet end of the housing;
a blower unit positioned at the outlet end of the housing and having an air inlet for receiving air flowing through the housing and an air exhaust for discharging air delivered to the blower unit inlet;
a plurality of free standing elongated tubular intake conduits each having an outlet end connected to the plenum and a free standing inlet end extending downwardly from the outlet end, the conduits being positioned in free standing relation in the second enclosed space in spaced relation to the side walls and the free standing inlet ends of the conduits being positioned at spaced locations proximate but spaced from the floor surface of the second enclosed space, the inlet ends being distributed over the entire area of the floor surface so as to effectively collect air from the entire second enclosed space proximate the floor surface in response to actuation of the blower unit; and
a source of radiant energy positioned to establish a fungi killing zone to intercept collected air moving through the intake conduits from the second enclosed air space into the inlet end of the blower unit.

26. A structure according to claim 25 wherein the source of radiant energy comprises ultraviolet lamp means.

27. A method of maintaining a building structure free of fungi, the building having an enclosed space within the structure defined by a floor surface, side walls and a ceiling, the method comprising the steps of:
providing a housing having an inlet end and an outlet end;
providing a blower at the outlet end of the housing having an inlet for receiving air flowing through the housing and an outlet for discharging air delivered to the blower inlet;
providing a plenum at the inlet end of the housing;
providing a plurality of elongated tubular intake conduits having outlet ends connected to the plenum and inlet ends extending downwardly from the outlet ends;
positioning the housing in an upper region of the enclosed space with the inlet ends of the conduits opening at spaced locations proximate the floor surface and distributed over the entire area of the floor surface whereby to effectively collect air from the entire enclosed space proximate the floor surface in response to operation of the blower and draw the collected air through the conduits and through the housing for delivery to the blower inlet;

subjecting the air flowing from the enclosed space to the blower to a germicidal treatment; and discharging the collected and germicidally treated air from the blower outlet;

the germicidal treating step comprising creating a fungi killing zone and passing the flow of air through the killing zone;

the enclosed space comprising a finished basement area of the building including paneling space from a foundation wall of the basement to define a dead air space between the foundation wall and the paneling;

the fungi killing zone being created in the dead air space.

28. A method of maintaining a building structure free of fungi, the building having an enclosed space within the structure defined by a floor surface, side walls and a ceiling, the method comprising the steps of:

providing a housing having an inlet end and an outlet end;

providing a blower at the outlet end of the housing having an inlet for receiving air flowing through the housing and an outlet for discharging air delivered to the blower inlet;

providing a plenum at the inlet end of the housing;

providing a plurality of elongated tubular intake conduits having outlet ends connected to the plenum and inlet ends extending downwardly from the outlet ends;

positioning the housing in an upper region of the enclosed space with the inlet ends of the conduits opening at spaced locations proximate the floor surface and distributed over the entire area of the floor surface whereby to effectively collect air from the entire enclosed space proximate the floor surface in response to operation of the blower and draw the collected air through the conduits and through the housing for delivery to the blower inlet;

subjecting the air flowing from the enclosed space to the blower to a germicidal treatment; and discharging the collected and germicidally treated air from the blower outlet;

the germicidal treating step comprising passing the flow of air through a fungi killing zone in which the flow of air is subjected to ultraviolet radiation;

the method including the further steps of providing a means for detecting the presence of a human in the enclosed space and extinguishing the ultra violet radiation in response to a sensed human presence.

29. An apparatus for abating fungi in a building structure having an enclosed space including side walls, a ceiling, and a floor surface, the apparatus comprising:

a housing having an inlet end and an outlet end;

a plenum defined at the inlet end of the housing;

a blower unit positioned at the outlet end of the housing and having an air inlet for receiving air flowing through the housing and an air exhaust for discharging air delivered to the blower unit inlet;

a plurality of elongated tubular conduits each having an outlet end communicating with the plenum and an inlet end extending downwardly from the outlet end, the conduits being configured such that, with the housing positioned in an upper region of the enclosed space, the inlet ends of the conduits are positioned at spaced locations proximate the floor surface, the inlet ends being distributed over the entire area of the floor surface, actuation of the blower unit being operative to effectively collect air from the entire area of the floor surface, draw it through the conduits to the plenum, and draw it through the housing for discharge into the enclosed space; and a source of radiant energy adapted to be positioned-to establish a fungi killing zone to intercept collected air moving through the conduits and the housing from the floor surface to the blower unit;

each intake conduit having a horizontal run connected to the plenum and a vertical run extending downwardly from the horizontal run to position the inlet end of the intake conduit proximate the floor surface of the enclosed space;

the source of radiant energy comprising a plurality of ultraviolet lamps adapted to be positioned in spaced relation in the enclosed space and operative to intercept the air moving into the intake ends of each of the intake conduits.

30. An apparatus according to claim 29 wherein the apparatus further includes means for sensing the humidity in the enclosed space and operative to actuate the blower unit and the radiant energy sources in response to variations in the sensed humidity.

* * * * *